(12) United States Patent
Stiefel et al.

(10) Patent No.: US 8,636,973 B2
(45) Date of Patent: Jan. 28, 2014

(54) METHOD OF PRODUCING PHARMACOLOGICALLY PURE CRYSTALS

(75) Inventors: Thomas Stiefel, Stuttgart (DE); Ortwin Kottwitz, Korntal-Munchingen (DE)

(73) Assignee: Biosyn Arzneimittel GmbH, Fellbach (DE)

( * ) Notice: Subject to any disclaimer, the term of this patent is extended or adjusted under 35 U.S.C. 154(b) by 0 days.

(21) Appl. No.: 13/805,684

(22) PCT Filed: Jun. 22, 2011

(86) PCT No.: PCT/EP2011/003099
§ 371 (c)(1),
(2), (4) Date: Feb. 27, 2013

(87) PCT Pub. No.: WO2011/160840
PCT Pub. Date: Dec. 29, 2011

(65) Prior Publication Data
US 2013/0149232 A1    Jun. 13, 2013

(30) Foreign Application Priority Data
Jun. 24, 2010 (EP) .................................. 10006596

(51) Int. Cl.
*A61K 9/14* (2006.01)
*A61K 33/04* (2006.01)
*B01D 9/00* (2006.01)
*B01J 8/18* (2006.01)
*C01B 19/00* (2006.01)

(52) U.S. Cl.
USPC ........ 423/508; 23/295 R; 23/302 T; 422/139; 422/245.1; 159/45; 159/DIG. 3; 159/DIG. 16

(58) Field of Classification Search
USPC .............. 423/508; 23/295 R, 302 T; 422/139, 422/245.1; 159/45, DIG. 3, DIG. 16
See application file for complete search history.

(56) References Cited

U.S. PATENT DOCUMENTS

| 4,190,622 | A | | 2/1980 | Landis | |
| 5,490,907 | A | * | 2/1996 | Weinwurm et al. | 203/29 |
| 5,674,617 | A | * | 10/1997 | Riemenschneider et al. | 428/402 |
| 6,680,032 | B1 | * | 1/2004 | Uhlemann et al. | 422/147 |
| 8,394,153 | B2 | * | 3/2013 | Eygelaar | 23/295 R |
| 2001/0022987 | A1 | | 9/2001 | Korfer et al. | |
| 2003/0088994 | A1 | | 5/2003 | Luethi et al. | |
| 2010/0028440 | A1 | | 2/2010 | Dobry et al. | |

FOREIGN PATENT DOCUMENTS

CN         101104520 A       1/2008

OTHER PUBLICATIONS

Database WPI Week 200869, Thomson Scientific, London, GB; AN 2008-L75065 (2008).
European Patent Office, International Search Report in International Patent Application No. PCT/EP2011/003099 (Aug. 4, 2011).

* cited by examiner

*Primary Examiner* — Timothy Vanoy
(74) *Attorney, Agent, or Firm* — Leydig, Voit & Mayer, Ltd.

(57) ABSTRACT

The present invention relates to means and methods for producing crystals or crystalline substances. In particular, crystals or crystalline substances which are useful as pharmaceutical ingredients can be manufactured.

19 Claims, 2 Drawing Sheets

METHOD OF PRODUCING PHARMACOLOGICALLY PURE CRYSTALS

CROSS-REFERENCE TO RELATED APPLICATIONS

This patent application is the U.S. national phase of International Patent Application No. PCT/EP2011/003099, filed Jun. 22, 2011, which claims the benefit of European Patent Application No. 10006596.0, filed Jun. 24, 2010.

The present invention relates to means and methods for producing crystals or crystalline substances. In particular, crystals or crystalline substances which are useful as pharmaceutical ingredients can be manufactured.

BACKGROUND

Crystallization is conventionally referred to as a process of the formation of solid crystals precipitating from a solution or melt or rarely deposited directly from a gas. Conventionally, the crystallization process consists of two major events, namely, nucleation and crystal growth. Nucleation is the step wherein the solid molecules disperse in the solvent start to form clusters on the nanometer scale. The stable clusters are denominated "nucleate". Whenever the clusters are not stable, they re-dissolve. In order for the clusters to become stable, they have to reach a critical size. The critical size depends on operating conditions such as temperature, supersaturation, etc. At a stage of nucleation, the atoms in the substance to be crystallized arranged in a defined manner that defines the crystal structure.

The term "crystal structure" refers to the relative arrangement of the atoms rather than the macroscopic properties of the crystal, which is in turn defined by parameters such as size and shape. The properties of the crystal are typically the result of the (internal) crystal structure.

Subsequent to the nucleation, the crystal growth occurs, which is the growth of a nucleate that succeeds in achieving the critical cluster size. The driving force of the crystallization process comprising nucleation and crystal growth is the supersaturation. The size of the crystals depends upon the conditions to either favour the nucleation or the growth of the nuclei. Once the supersaturation is exhausted, the solid liquid system reaches the equilibrium and the crystallization process is complete. The operation conditions can be modified from the equilibrium so as to supersaturate again.

Many compounds have the ability to crystallize with different crystal structures, a phenomenon called polymorphism. Each polymorph represents a different thermodynamic solid state and crystal polymorphs of the same compound exhibit different physical properties, e.g., the solution rate, shape, melting point, etc. Polymorphism is of a major importance in industrial manufacture of crystalline products.

Crystallization may be used in the industry in order to provide highly purified products, in order to obtain salts or other crystalline end products.

For a crystallization, or re-crystallization to occur from a solution, the solution must be supersaturated. This means that the solution has to contain more solute entities (molecules or ions) dissolved that it would contain under the equilibrium, i.e., the saturated solution. Supersaturated conditions can be achieved by various methods such as solution cooling, addition of secondary solvents to reduce solubility of the solute (antisolvent or drown out technique), chemical reaction or change in pH. All of these methods are employed in industrial practice. Also, solvent evaporation can be used.

Figure 1:
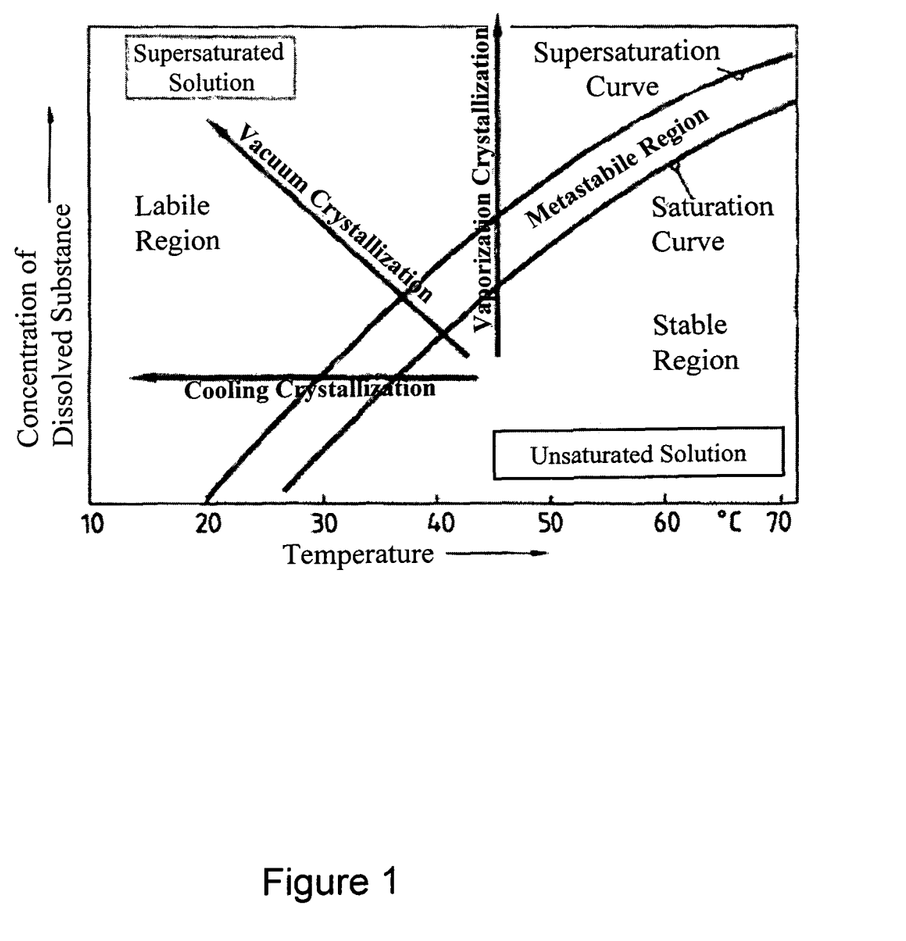
FIG. 1 exhibits a saturation curve, i.e. graph, which shows the borderline between unsaturated and supersaturated solution.

FIG. 1 exhibits a saturation curve, i.e. graph, which shows the borderline between unsaturated and supersaturated solution. In practice, between the saturation curve and the supersaturation curve, a so-called meta-stable region occurs. Between the saturation curve and the supersaturation curve, a spontaneous crystallization of the solid takes place in this meta stable region. In order to enter the left-handed region, i.e., the supersaturated solution, the temperature may be rapidly decreased without changing the amount of substance per volume of solution (so-called cooling crystallization), the amount of substance per volume of solvent may be rapidly increased at a constant temperature, e.g., by vaporization (so-called vaporization crystallization), or both temperature and amount of substance per volume of solvent are rapidly changed simultaneously, i.e. the temperature is decreased, while the amount of substance per volume is increased (so-called vacuum crystallization). Once a simple saturated solution is obtained, a seed crystal is then introduced in order to induce the crystallization process.

Conventional industrial equipment for crystallization makes use of cooling crystallization, vaporization crystallization and vacuum crystallization.

One example for vaporization crystallization equipment is the so-called circulating liquid evaporator crystallizer. The circulating liquid is drawn by a screw pump down inside the tube side of the condensing stream heater. The heated liquid then flows into the vapour space where flash evaporation occurs resulting in supersaturation. The vapour leaving is condensed. The supersaturated liquid flows down the downflow tube and then up through the bed of fluidized and agitated crystals. The crystals grow in size. The leaving saturated liquid then goes back as a recycle stream to the heater where it is joined by the entering fluid. The larger crystals settle out and the slurry of crystals and mother liquid is withdrawn as a product.

An example for cooling crystallization is realized in classical tank crystallizers. Saturated solutions are allowed to cool in open tanks. After a period of time, the mother liquid is drained and the crystals are removed.

One example for a vacuum crystallizer is the so-called circulating magma vacuum crystallizer. A suspension (magma) of crystals is circulated out of the main body of the apparatus through a circulating pipe by a screw pump. The magma flows through a heater where the temperature is raised. The heated liquid then mixes with body slurry and boiling occurs at the liquid surface. This causes supersaturation in the swirling liquid near the surface, which deposits in the swirling suspended crystals until they leave again via the circulating pipe. The vapours leave through the top. A steam jet ejector provides a vacuum.

While these classical crystallization methods employ seed crystals for initiating the crystallization process, other methods have been described, wherein nucleation and crystal growth are initiated without the need for seed crystals. DE 60310923 describes the production of crystals using high power ultra sound. The method is in particular useful for the production of highly pure crystals under aseptic conditions. Highly purified products to be produced under aseptic conditions normally lack the presence of seed crystals since both solution and surfaces of the production apparatus are too clean to allow the presence of seed crystals.

Hydrates are inorganic or organic substances that contain crystal bound water. The water molecules are combined with the molecule in a definite ratio as an integral part of the crystal. The notation of hydrate compounds is "$nH_2O$", wherein n is the number of water molecules per molecule of salt. "n" is usually a low integer although it is possible that fractioned values exist. In a monohydrate n is 1; in a hexahydrate n is 6, etc.

The stability of hydrates is generally determined by the nature of the compounds, their temperature and the relative humidity if they are exposed to an open surrounding. Inorganic and organic compounds exist in various hydrates.

One example is sodium selenite ($Na_2SeO_3$), which exists in an unhydrated form (without crystal bound water) as a pentahydrate $Na_2SeO_3 \times 5H_2O$) as well as an octahydrate ($Na_2SeO_3 \times 8H_2O$). The crystallization of highly purified species is not possible using conventional crystallization processes, in particular when the high purity standards have to be met. Given the lability of the various hydrates, it is in particular necessary to work under precise conditions in order to obtain a homogenous composition of precisely defined crystal water content, i.e., a composition which does not contain too much bound crystal water nor suffers from loss of crystal water.

Sodium selenite pentahydrate is listed in the monographs of European pharmacopeia (Ph. Eur. 1677) and in order to fulfil the restrictive standards of the pharmacopeia, the active substance approved as a pharmaceutical has to fulfil all requirements given in the monograph.

Janitzki et al., Über die selenig säuren Salze des Natriums und des Kaliums. Zeitschrift für Anorganische und allgemeine Chemie 205 (1932):49-75 describes sodium selenic pentahydrate to be stable between −8.7° C. and 39.5° C. Below the temperature range the octahydrate exists whereas above 38.5° C., the anhydrous material is stable. Conventionally, sodium selenic pentahydrate for the pharmaceutical field was produced employing evaporation and cooling techniques.

Unfortunately, the production of highly purified sodium selenite pentahydrate meeting the standards of the pharmacopeia is incompletely described in the prior art, hardly reproducible and does not meet the GMP Guidelines for the manufacturing of Active Pharmaceutical Ingredients (API's).

Sodium selenite pentahydrate is a good example that there is a need in the field for a new manufacturing process for well-defined and highly pure crystals, preferably useful in the pharmaceutical field.

SUMMARY OF THE INVENTION

The present inventors facing the problem of the provision of sodium selenite pentahydrate meeting the standards of the pharmacopeia, in particular for the application in parenteral preparations, have provided such a new production process as well as a corresponding device, which are the results of a sophisticated research program, i.e. a highly laborious process, in which several unexpected experimental difficulties had to be overcome. The details of the research program are shown in Example 1.

Surprisingly, the new method and corresponding new apparatus allows the manufacturing of crystalline products in one closed apparatus under ultra clean and aseptic conditions. The new manufacturing process as well as the new apparatus are therefore not limited to the production of sodium selenite pentahydrate, but open a new possibility for the reliable and pharmaceutical manufacturing of highly pure ("first class") crystals.

According to the present invention, a manufacturing process is provided which comprises spraying an unsaturated solution of a substance to be crystallized into a fluidized bed dryer under conditions of applying a vacuum of a particular range and maintaining a certain temperature range. The vacuum is applied in a manner in order to obtain a supersaturated solution while the temperature is simultaneously regulated within a previously defined temperature range in which the crystalline product is stable. Both the vacuum and temperature conditions are chosen so that vaporization crystallization is achieved. Preferably, the method does not contain the addition of a seed crystal.

According to a preferred embodiment, the unsaturated solution is sprayed into a mechanically created fluidized bed, wherein the crystallization takes place under agitation. Under these conditions a mechanically induced crystallization takes place which leads to an ultra homogenous substance of a reproducible stability.

Once the amount of solution has been sprayed into the fluidized bed dryer, or preferable the mechanically created fluidized bed, temperature and vacuum are still regulated in order to end up with the dried product, i.e. the product which is within the specifications required.

The present invention also provides a device for manufacturing a crystalline substance, which comprises
 a) a fluidized bed dryer in a vacuum vessel,
 b) inlet means for transporting an unsaturated solution of the raw substance to be crystallized into the vacuum vessel,
 c) means for temperature regulating,
 d) a spraying device for introducing the unsaturated solution into the fluidized bed dryer; and
 e) outlet means for transporting vapour out of the vacuum vessel; and
 f) discharge means for removing the crystalline substance out of the vacuum vessel.

Figure 2:
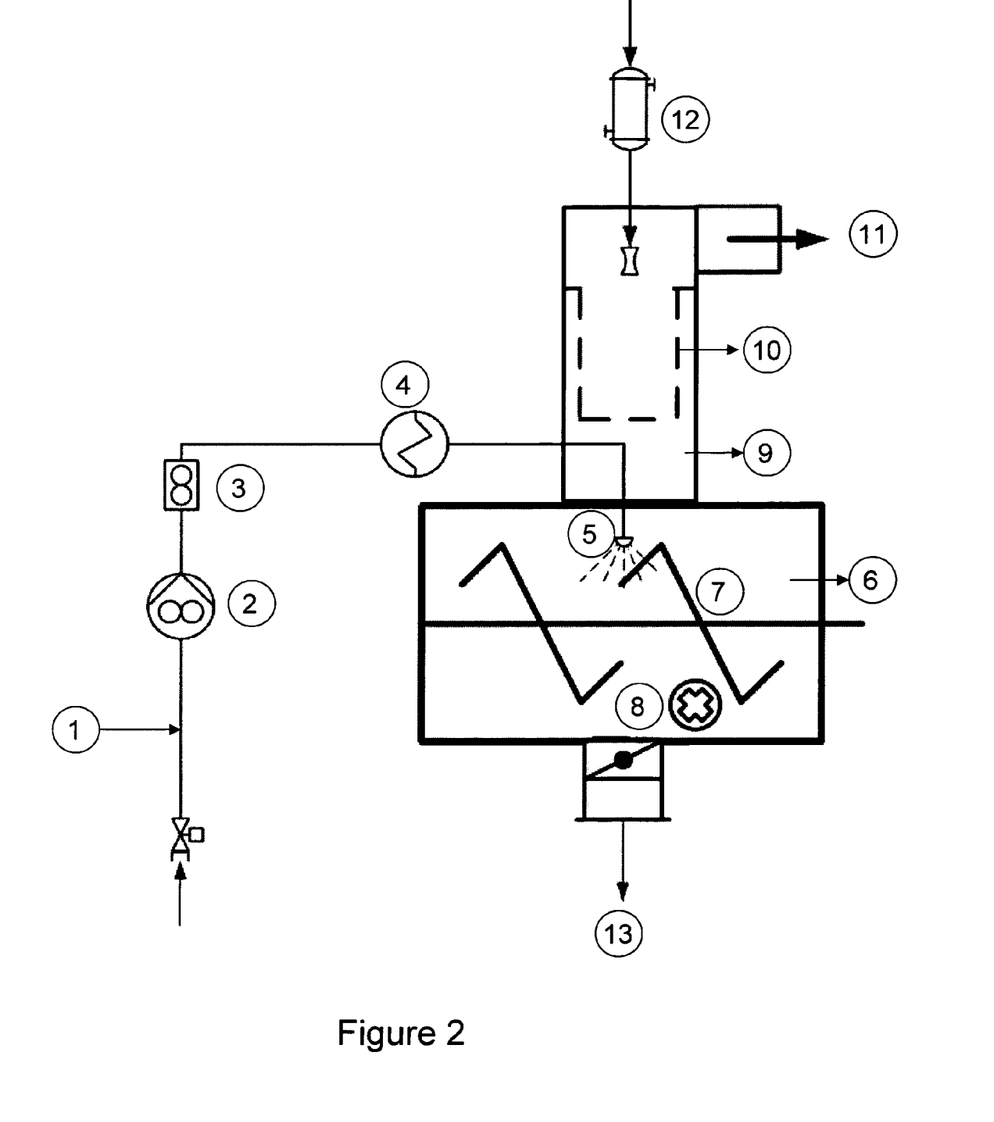

In a preferred embodiment, the device of the present invention comprises a vacuum vessel (6), which may be double walled, with one or more mixing elements (7, 8), here two paddle stirrers, a vapour dome housing (9) with pulse back dust filter (10), a nitrogen supply (12), an optional air filter (not shown), a spraying nozzle (5), a heat exchanger (4), a flow meter (3), a feed pump (2), and a pipe to the vacuum pumping unit (1).

FIG. 2 shows this device. In the device, the unsaturated solution is pumped (2) through the feed piping (1), controlled by a flow meter (3), heated by a heat exchanger (4) and finally injected into the vacuum vessel (6) by means of a spraying nozzle (5). Evaporation of the solvent leads to supersaturation of the injected solution. Crystallisation takes place spontaneously under formation of a fluidized bed, created by agitation employing the mixing elements (7, 8). The vapour is exhausted through the vapour dome housing (9) with the built-in pulse back dust filter (10) and the vacuum piping (11). The pulse back dust filter is operated in regular intervals using filtered nitrogen (12) to prevent filter blockage. After completion of the crystallization and drying process the crystallized product is removed through the discharge door (13).

Definitions

Within the present invention technical terms are used in their meaning which is established in the art. The terms below are particularly defined as follow.

A "fluidized bed" is formed when a quantity of a solid particulate substance (usually present in a holding vessel) is placed under appropriate conditions to cause the solid/fluid mixture to behave as a fluid. This is usually achieved by the introduction of pressurized fluid through the particulate medium. This results in the medium then having many properties and characteristics of normal fluids; such as the ability to free-flow under gravity, or to be pumped using fluid type technologies.

A "fluidized bed dryer" is an apparatus basically comprising a cylindrical vessel with a conical designed bottom part. The fluidized bed is here generated via providing compressed air and furnishing a particle-forming substance.

By applying top or bottom spray techniques a dissolved substance can be sprayed on the fluidized bed in the methods of the present invention. The solvent will be removed by evaporation by means of heating the compressed air. Integrated dust filter in the exhaust gas flow prevent from discharge of the product. Parameters e.g. temperature and flow of the feed solution and the compressed air as well as the temperature the product may be controlled and measured.

A "mechanically created fluidized bed dryer" is an apparatus basically comprising a vessel for heating and cooling with integrated mixing elements. Due to agitating or mixing these elements create the mechanically created fluidized bed in situ.

In the present invention, the mechanically created fluidized bed is created while spraying a dissolved substance. The solvent will be removed preferably applying vacuum to accelerate the evaporation. The vapor is diverted through a pulse dust filter operated with nitrogen or compressed air, respectively. Parameters e.g. temperature and flow of the feed solution as well as the temperature of the product and the pressure in the vessel may be controlled and measured.

FIGURES

FIG. 2 shows a device of a preferred embodiment of the present invention. In the device, the unsaturated solution is pumped (2) through the feed piping (1), controlled by a flow meter (3), heated by a heat exchanger (4) and finally injected into the vacuum vessel (6) by means of a spraying nozzle (5).

DETAILS OF THE INVENTION

Embodiments of the invention are:

1. A process for manufacturing a crystalline substance comprising the steps of
   a) delivering an unsaturated solution of the substance to be crystallized into a fluidized bed dryer under conditions of applying a vacuum, i.e. the pressure is below 1 bar, and maintaining a temperature range, in order to dry the solution of a substance to be crystallized to thereby obtain a supersaturated solution, in which crystallization takes place ("initiation of crystal formation", "crystal pulp phase"),
   b) applying vacuum and maintaining a temperature range in the fluidized bed dryer after completion of the step of delivering the unsaturated solution of the substance to be crystallized, wherein the vacuum and the temperature are regulated in a manner in order to obtain the desired crystalline product as a homogenous product ("powder formation").
2. The process of embodiment 1, wherein the method does not contain a step of adding a seed crystal.

The seed crystals of this embodiment form in situ.

3. The process of embodiment 1 or 2, wherein in step a) the unsaturated solution is delivered by spraying, pumping or sprinkling, preferably by spraying.
4. The process of any of embodiments 1 to 3, wherein the unsaturated solution of the substance to be crystallized is delivered into a fluidized bed dryer, which is a mechanically created fluidized bed dryer, wherein the crystallization takes place under mechanical agitation.
5. The process of any of embodiments 1 to 4, wherein the crystalline substance obtained is of high purity, preferably of more than 90%, 95%, 96%, 97%, 98%, 99%, 99.9%, 99.99%, 99.999%, 99.9999% purity.
6. The process of any of embodiments 1 to 5, wherein the crystalline substance is a pharmaceutical product, preferable one which meets the requirements of the Pharmacopeia.
7. The process of any of embodiments 1 to 6, wherein the crystalline substance is an inorganic or organic salt, preferably a selenium salt, more preferable a hydrate of $Na_2SeO_3$, most preferable $Na_2SeO_3 \times 5\ H_2O$.
8. The process of any of embodiments 1 to 7, wherein the crystalline substance is a hydrate.
9. The process of any of embodiments 1 to 8, preferably of embodiments 7 to 8, wherein the humidity is controlled in step a) and b).
10. The process of any of embodiments 1 to 9, wherein the temperature and/or vacuum are controlled in step a) and b).
11. The process of embodiment 10, wherein the temperature and/or vacuum are controlled in step a) and b) in order to avoid sticking of dry substance to the surface of the fluidized bed dryer.
12. The process of any of embodiments 1 to 11, further comprising one or two steps of
    c) adding an amount of free solvent into the fluidized bed dryer, and/or
    d) regulating pressure and temperature before removing the crystalline substance from the fluidized bed dryer.
13. The process of any of embodiments 1 to 12, wherein the temperature is kept in a range between −10° C.-+125° C.

Preferably in step a) the temperature is kept in a range −10° C. to +100° C., in step b) between −10° C. and +125° C. and in step c) between 0° C. and +125° C.

These conditions depend from the chemical nature of the substance to be crystallized.

For $Na_2SeO_3 \times 5\ H_2O$ the ranges are preferably as follow: a) 22° C.-26° C.; b) 20° C.-30° C.; c) 26° C.-30° C.

14. The process of any of embodiments 1 to 13, wherein the vacuum is kept in a range between 2 mbar-100 mbar.

Preferably in step a) the vacuum is kept between 6.5 mbar and 100 mbar, in step b) between 8 mbar and 100 mbar and in step c) between 6.5 mbar and 100 mbar.

For $Na_2SeO_3 \times 5\ H_2O$ the ranges are preferably as follows: a) 6.5 mbar-9 mbar; b) 10 mbar-6 mbar; c) 14.5 mbar-16.5 mbar.

15. The process of any of embodiments 1 to 14, wherein the water content is kept in a range between 80% and 0%, preferably between 80% and 5%.

Preferably in step a) the water content is kept between 80%-0%, in step b) between 80-0% and in step c) between 80%-0%.

For $Na_2SeO_3 \times 5\ H_2O$ the ranges are preferably as follows: a) 70%-40%; b) 50%-32%; c) 60%-40%.

16. The process of any of embodiments 1 to 15, wherein the ratio between the volume of the unsaturated solution of the substance to be crystallized and the fluidized bed dryer is kept in a range between 1:4-2:1, more preferably 1:1.

The volume of fluidized bed dryer is the volume of the vacuum vessel, in which the fluidized bed is created.

17. The process of any of embodiments 1 to 16, wherein temperature and vacuum of step a) temp are set in the fluidized bed dryer before performing step a).

18. The process of any of embodiments 1 to 17, wherein the delivering velocity is regulated depending from the amount of substance already delivered.
19. The process of any of embodiments 1 to 18, wherein the time in step b) is controlled by adjusting the vacuum within a range of 7.5-100 mbar.
20. The process of any of embodiments 1 to 18, wherein one or more of steps a) to d) are performed under inert gas.
21. The process of any of embodiments 1 to 19, wherein before step a) is performed, a step of forming the unsaturated solution is performed, in which the substance to be crystallized is dissolved in the solvent, and/or one or more purification steps are performed in solution.
22. Use of the process of any of embodiments 1 to 20 for producing a crystalline substance, preferably a pharmaceutical.
23. A device for manufacturing a crystalline substance, which comprises
    a. a fluidized bed dryer in a vacuum vessel,
    b. inlet means for transporting an unsaturated solution of the raw substance to be crystallized into the vacuum vessel,
    c. means for temperature regulating,
    d. a device for introducing the unsaturated solution into the fluidized bed dryer; and
    e. outlet means for transporting vapour out of the vacuum vessel; and
    f. discharge means for removing the crystalline substance out of the vacuum vessel.

Preferably the means for introducing the unsaturated solution into the fluidized bed dryer is a spraying device. Other (equivalent) means are sputtering, nebulising or sprinkling devices.

24. The device of embodiment 24, wherein the fluidized bed dryer is a mechanically induced fluidized bed dryer, preferably comprising one or more mixing elements (7, 8), e.g. one or more paddle stirrers and/or one or more multiple choppers.
25. The device of embodiment 23 or 24, wherein the inlet means comprises a feed piping (1), a feed pump (2) and/or a flow meter (3).
26. The device of embodiment 23, 24 or 25, wherein the spraying device comprises one or more nozzles (5).
27. The device of any of embodiments 23 to 26, wherein the outlet means comprise a vapour dome housing (9), a built-in pulse back dust filter (10), a vacuum pipe to a vacuum pump (11) and/or a nitrogen supply (12).
28. The device of any of embodiments 23 to 27, wherein the discharge means is a discharge door (13).
29. The device of any of embodiments 23 to 28, wherein the means for temperature regulating comprises a heat-exchanger (4) and/or a heat transfer medium being part of the double walled vacuum vessel.
30. The device of any of embodiments 23 to 29 further comprising means for measuring temperature, pressure and humidity in the vacuum vessel.
31. Use of the device of any of embodiments 23 to 30 for producing a crystalline substance, preferably a pharmaceutical.

In the methods, uses and devices of the above embodiments of the present invention, the following crystallization and drying parameters may be set. These parameters have been established and set by the inventors based on and/or depending from the physico-chemical properties of the crystalline substance to be produced.

In order to minimize evaporation time of the solvent as well as the required energy, the concentration of the feed solution (i.e. the unsaturated solution) of the substance to be crystallized has to be adjusted as close as possible to the saturation point. The evaporation time of the solvent and removal of the undesired residual water is determined by the exhausting rate of the vacuum pumping unit and the preset temperature of the unsaturated solution.

During the spraying phase of the unsaturated solution the crystallization temperature of the achieved supersaturated solution is preferably controlled by the flow rate of the feed solution, the temperature of the heat exchanger, the selected temperature of the heat transfer medium of the double walled vacuum vessel and the applied vacuum conditions. Thus this complex control mechanism allows to generate the accurate crystallization conditions even for very temperature sensitive hydrates.

The velocities of the mixing elements (paddle stirrer, multiple chopper) may be selected and coordinated in order to generate the mechanically created fluidized bed for the crystallisation phase, followed by further adjustment to apply the required velocities during the post drying phases in order to remove residual free water. For the initial crystallization phase and during injection of the complete feed solution the velocity for the paddle stirrer may preferably be adjusted within a range of 20 rpm-80 rpm and for the multiple chopper preferably within a range of 200 rpm-400 rpm. Post drying phases require intermittent velocities, preferably between 30 rpm-150 rpm for the paddle stirrer and preferably 300 rpm up to 3000 rpm for the multiple chopper.

Based on the above described basic conditions and parameters the crystallization and drying process for $Na_2SeO_3 \times 5 H_2O$ has been established. One preferred embodiment of said crystallization process is described below:

The $Na_2SeO_3$ feed solution is adjusted to approx. 29-31% (g/g) dry substance content. The crystallization and drying process comprises the following process steps:

1. Initial Crystallization Phase

Spraying of approx. 1 kg feed solution intermittently at approx 130 g/min in a pressure range of 6.5-9.0 mbar. The Temperature of feed solution is approx. 90° C., the chamber temperature approx. 24° C. The velocities of the mixing elements are: paddle stirrer at approx. 60 rpm; multiple chopper at approx. 300 rpm.

2. Main Crystallization Phase

Step 1: Spraying of approx. 1.5 kg feed solution intermittently at approx 160 g/min, in a pressure range 7.5-10.0 mbar. The temperature of the feed solution is approx. 75° C., the chamber temperature approx. 24° C. The velocities of the mixing elements are: paddle stirrer approx. 60 rpm; multiple chopper approx. 300 rpm.

Step 2: Spraying of approx. 2.5 kg feed solution intermittently at approx. 160 g/min, in a pressure range 8.0-11.0 mbar. The Temperature of the feed solution is approx. 75° C., the chamber temperature approx. 24° C. The velocities of the mixing elements are: paddle stirrer approx. 60 rpm; multiple chopper approx. 300 rpm.

Step 3: Spraying of approx. 2.5 kg feed solution intermittently at approx. 160 g/min, in a pressure range 9.0-12.0 mbar. The temperature of the feed solution is approx. 75° C., the chamber temperature is approx. 24° C. The velocities of the mixing elements are: paddle stirrer approx. 60 rpm; multiple chopper approx. 300 rpm.

Step 4: Spraying of approx. 2.5 kg feed solution intermittently approx. 160 g/min, in a pressure range 9.5-12.0 mbar. The temperature of the feed solution is approx. 75° C., the chamber temperature is approx. 24° C. The velocities of mixing elements are: paddle stirrer approx. 60 rpm; multiple chopper approx. 300 rpm.

Step 5: Spraying of approx. 2.5 kg feed solution intermittently approx. 160 g/min, in a pressure range 10.5-12.5 mbar. The temperature of the feed solution is approx. 75° C., the chamber temperature is approx. 24° C. The velocities of mixing elements are: paddle stirrer approx. 60 rpm; multiple chopper approx. 300 rpm.

Step 6: Spraying of approx. 2.5 kg feed solution intermittently approx. 160 g/min, in a pressure range 11.0-13.0 mbar. The temperature of the feed solution is approx. 75° C., the chamber temperature is approx. 24° C. The velocities of mixing elements are: paddle stirrer approx. 60 rpm; multiple chopper approx. 300 rpm.

Step 7: Spraying of approx. 2.5 kg feed solution intermittently approx 160 g/min, in a pressure range 12.5-14.5 mbar. The temperature of the feed solution is approx. 75° C., chamber temperature is approx. 28° C. The velocities of mixing elements are: paddle stirrer approx. 60 rpm; multiple chopper approx. 300 rpm.

Step 8: Spraying of approx. 2.5 kg feed solution intermittently approx 160 g/min, in a pressure range 13.5-15.5 mbar. The temperature of the feed solution is approx. 75° C., the chamber temperature is approx. 28° C. The velocities of mixing elements are: paddle stirrer approx. 60 rpm; multiple chopper approx. 300 rpm.

Step 9: Spraying of approx. 2.5 kg feed solution intermittently approx. 160 g/min, in a pressure range 14.0-16.0 mbar. The temperature of the feed solution is approx.75° C., chamber temperature approx. 28° C. The velocities of mixing elements are: paddle stirrer approx. 60 rpm; multiple chopper approx. 300 rpm.

Step 10: Spraying of approx. 2.5 kg feed solution intermittently approx 160 g/min, in a pressure range 14.5-16.5 mbar. The temperature of the feed solution is approx. 75° C., chamber temperature approx. 28° C. The velocities of mixing elements are: paddle stirrer approx. 60 rpm; multiple chopper approx. 300 rpm.

Step 11: Spraying of approx. 2.5 kg feed solution (remaining solution) and flushing with approx. 200 g of free solvent intermittently approx 160 g/min, in a pressure range 14.5-16.5 mbar. The temperature of the feed solution is approx. 75° C., chamber temperature approx. 28° C. The velocities of mixing elements are: paddle stirrer approx. 50 rpm; multiple chopper approx. 300 rpm.

3. Post Drying Phase

Step 1: The pressure is controlled at 16.5-8.0 mbar. The chamber temperature is approx. 24° C. The velocities of mixing elements are: paddle stirrer approx. 40 rpm; multiple chopper approx. 300 rpm.

Step 2: The time controlled is 5 min. The chamber temperature is approx. 22° C. The velocities of mixing elements are: paddle stirrer approx. 90 rpm; multiple chopper approx. 3000 rpm.

Step 3: The time controlled is 10 min. The chamber temperature is approx. 22° C. The velocities of mixing elements are: paddle stirrer approx. 60 rpm; multiple chopper approx. 1000 rpm.

Step 4: The time controlled is 15 min. The chamber temperature is approx. 22° C. The velocities of mixing elements are: paddle stirrer approx. 90 rpm; multiple chopper approx. 1500 rpm.

Step 5: Sampling under atmospheric pressure. The chamber temperature is approx. 22° C. The velocities of mixing elements are: paddle stirrer approx. 40 rpm; multiple chopper approx. 300 rpm.

Step 6: Optionally repeat step 4, when loss of drying is >34%.

EXAMPLES

Example 1

Production of $Na_2SeO_3 \times 5\ H_2O$

This example shows the efforts undertaken by the present inventors in order to establish the manufacturing process for sodium selenite pentahydrate ($Na_2SeO_3 \times 5\ H_2O$) for its use as active pharmaceutical ingredient (API) in oral and parenteral preparations.

1. Synthesis of Sodium Selenite

In a first evaluation phase the conceptual design of the production process was established taking into consideration the following basic conditions: synthesis of sodium selenite, purification from inorganic and organic contaminants, formation of crystal water during crystallization and drying.

The synthesis takes place according to the chemical reaction indicated below. As starting material selenium dioxide ($SeO_2$) was selected.

$$SeO_2 + H_2O \rightarrow H_2SeO_3 \text{ (selenious acid)}$$

$$H_2SeO_3 + 2\ NaOH \rightarrow Na_2SeO_3 + 2\ H_2O$$

Due to the intended final batch size of approx. 10 kg $Na_2SeO_3 \times 5\ H_2O$ the required quantity of $SeO_2$ was calculated taking into account its solubility in water and the final concentration of sodium selenite ($Na_2SeO_3$) after the reaction with sodium hydroxide (NaOH). Thus approx. 38 mol of $SeO_2$ was determined to be needed for one batch. The solubility of $SeO_2$ is 0.384 kg/l $H_2O$ (14° C.). Considering the $Na_2SeO_3$ content of approx. 30% (m/m) designated for the solution which will be introduced into the crystallization/drying process the concentration of the starting solution for the synthesis was set to 2.5 mol/l (0.281 kg/l), Based on the conceptual design and the basic calculations the experimental development was carried out employing in parallel the purification part and the crystallization/drying trials.

2. Purification Part 1: Elimination of Heavy Metal Impurities

The starting material $SeO_2$ may contain heavy metal impurities, which would also be found in a certain concentration level in the API $Na_2SeO_3 \times 5H_2O$.

The whole spectrum (As, Cd, Fe, Cu, Ni, Te, Hg, Pb and Ag) of heavy metal impurities relevant as potential contaminants originated from $SeO_2$ have been specified in terms of limits for the single elements. Due to the limits of heavy metals set for the API it has been concluded to develop an efficient removal step.

Pre-selection of suitable ion-exchange resins showed that their pH working area is situated between pH 1.5-9. However complete reaction of $SeO_2$ and NaOH to $Na_2SeO_3$ leads to pH values above 10. For that reason the metal depletion should be carried out employing sodium hydrogen selenite ($NaHSeO_3$) solution around pH=6.

Based on this evaluation the synthesis has to be carried out in two steps according to the chemical reactions below:

Step 1—pH =6:

$$SeO_2 + H_2O + NaOH \rightarrow H_2SeO_3 + NaOH \rightarrow NaHSeO_3 + H_2O$$

Step 2—pH=10:

$$NaHSeO_3 + NaOH \rightarrow Na_2SeO_3 + H_2O$$

a) Synthesis Step 1: Preparation of Starting Solutions

In order to determine physical-chemical parameters (density, pH value) lab scale batches (100 ml) of $H_2SeO_3$ solutions were prepared by dissolving crystalline $SeO_2$ (0.25 mol) in water (concentration 2.5 mol/l). Subsequently NaOH pellets were added up to pH 6.0.

The $H_2SeO_3$ solutions were tested on density and pH with results as follows:

pH-value ($H_2SeO_3$): pH==1.3 density ($H_2SeO_3{}_{(aq)}$): d=1.22 g/cm³ amount of NaOH-pellets needed to reach pH=6: m=10.5 g (n=0.26 mol).

Based on the results obtained from the lab scale batches up-scaling was performed for the preparation of $H_2SeO_3$ solution to be used in the metal depletion trials.

Preparation of the $H_2SeO_3$ Solution:

In a first step two batches of 15 liter of $H_2SeO_3$ solution were prepared. The final batch weight of 18.3 kg was calculated by means of the density identified from the lab scale batches.

Following Biosyn's production policy disposable materials have been already used during development wherever possible.

The preparation was carried out under a laboratory hood. A 50 liter tank liner was stabilized by using a 25 liter cylindrical plastic container. The container was placed on a balance and set to zero. 10 kg purified water were transferred into the tank liner. A total of 4.22 kg $SeO_2$ was added to the purified water by using a plastic beaker. The $SeO_2$ was added in 3 portions, each of approx. 1.4 kg. The $SeO_2$ was dissolved by stirring (approx. 400 rpm). After complete dissolution of the $SeO_2$, purified water was added to reach the final batch weight of 18.3 kg (15 liters). This solution was prepared twice. A sample of each preparation was taken for further analysis.

Both batches were filtered into a 50 liter Flexboy$^R$ bag using a pre-filter Polysep II, Opticap XL2, 1/0.5 .tm. A part of the pre-filtered solution (approx. 5.2 kg/4.3 liter) was sterile filtered under laminar flow into a 5 liter Flexboy bag. A sample was taken for analysis. The $H_2SeO_3$ solution was kept as backup material for the metal depletion trials. The remaining solution was taken for the preparation of the $NaHSeO_3$ solution.

Preparation of the $NaHSeO_3$ Solution:

The preparation was carried out under a laboratory hood. The remaining $H_2SeO_3$ solution (approx. 31.4 kg; 25.7 liter) was pumped into a new tank liner. A total of 2.60 kg NaOH pellets were added by using a plastic beaker. The addition was carried out in approx. 250 g portions.

The NaOH pellets were dissolved by stirring (approx. 400 rpm). NaOH pellets were added until a pH-value of 6.1 was reached. For the pH measurement, samples were taken out of the tank liner after the addition of 2 kg (pH=3.0), 2.5 kg (pH=5.2) and 2.60 kg (pH=6.1) NaOH pellets. During, addition of the NaOH pellets, the temperature of the solution was directly controlled by using a Pt-100 temperature sensor. The temperature reached a maximum of 78° C. The final batch weight was approx. 34 kg (28 liter, calculated after determination of density). The hot solution was sterile filtered under laminar flow into a new 50 liter Flexboy bag (pump flow 1 l/mm). A sample was taken for analysis.

The $H_2SeO_3$ solution and the $NaHSeO_3$ solution were tested on pH density and conductivity also in order to establish future IPC parameter.

TABLE 1

(all parameters were measured at 20° C.):

| Sample | pH | Density (g/cm³) | Conductivity (mS/cm) |
|---|---|---|---|
| $H_2SeO_3$ preparation # 1 | 0.8 | 1,218 | 47 |
| $H_2SeO_3$ preparation # 2 | 0.8 | 1,220 | 48 |
| $H_2SeO_3$ pooled solution | 0.8 | 1,220 | 48 |
| $NaHSeO_3$ | 5.8[1] | 1,282 | 72 |

[1] the pH-value of 6.1 was measured in the hot solution. The difference was caused by the large temperature compensation of the pH-meter.

b) Metal Depletion

The aim of this step was the development of the elimination of heavy metal impurities from a $NaHSeO_3$ solution at pH=6. Table 2 below shows the specification for $SeO_2$ in comparison to the specification of the API $Na_2SeO_3 \times 5\ H_2O$.

Based on the limits for the metals shown in Table 2 the required elimination capacity was calculated. The basis of the calculation was that 2.43 mol/l $NaHSeO_3$ solution was prepared from a 2.50 mol/l $HSeO_3$ solution.

In Table 3 below the maximum metal values allowed in the NaHSeO3 solution have been calculated in relation to the limits set for the API $NaSeO_3 \times 5\ H_2O$.

TABLE 2

| Metal | Specification $SeO_2$ (mg/kg) | Specification $Na_2SeO_3 \times 5H_2O$ (mg/kg) |
|---|---|---|
| As | ≤20 | ≤20 |
| Cd | ≤5 | ≤5 |
| Fe | ≤50 | ≤10 |
| Cu | ≤10 | ≤5 |
| Ni | ≤10 | ≤5 |
| Te | ≤500 | ≤300 |
| Hg | ≤5 | ≤5 |
| Pb | ≤50 | ≤5 |
| Ag | ≤10 | ≤5 |

TABLE 3

| Metal | Max. values in $NaHSeO_3$ (calculated from $SeO_2$ spec.) (mg/kg) | Limits $NaHSeO_3$ (calculated from $Na_2SeO_3 \times 5H_2O$ spec.) (mg/kg) | Required removal (mg/kg) |
|---|---|---|---|
| As | 4.20 | 12.80 | 0 |
| Cd | 1.05 | 3.20 | 0 |
| Fe | 10.5 | 6.40 | 4.10 |
| Cu | 2.10 | 3.20 | 0 |
| Ni | 2.10 | 3.20 | 0 |
| Te | 105 | 192 | 0 |
| Hg | 1.05 | 3.20 | 0 |
| Pb | 10.5 | 3.20 | 7.30 |
| Ag | 2.10 | 3.20 | 0 |

The comparison of the maximal achievable metal values with the maximal allowed metal values showed that only the removal of iron and lead might be necessary, depending on the specified limits for the metal impurities in $SeO_2$. However in terms of robustness of the whole manufacturing process and potential changing (possible increases) of metal contents, a reduction of the other metals during metal depletion is beneficial for the entire process.

Three different types of resins filled in columns to 100 ml each were tested on heavy metal elimination from the NaHSeO$_3$ starting solution:

E 33 HC—iron oxide/hydroxide adsorbent
P 7121—macro porous selective ion exchanger, chelating iminodiacetic acid as functional group
P 7122—mono spheric, macro porous metal chelating resin, thiourea as functional group The NaHSeO$_3$ solution was spiked with heavy metals to evaluate the elimination. The upper specification limit for each metal in SeO2 was taken as a measure for the metal salt addition, but the analysis of this solution has shown, that in most cases the specification limit could not have been reached. This is caused by the solubility limits of the salts. The analysis was performed by ICP-OES (inductive coupled plasma-optical emission spectrum).

The obtained test results showed that the resin P 7121 was able to reduce all metals significantly with the exception of As and Te. The resin E 33 HC was able to reduce all metals with the exception of Fe. The iron concentration increased after the column, because of fine eroded solid particles of the iron oxide/hydroxide adsorbent. The selective resin P 7122 revealed to be unsuitable in this metal elimination application. Finally the results and related aspects considered lead to the conclusion, that the resin P 7121 is the best suited material for removal of heavy metals from NaHSeO$_3$ solutions.

Scale Up—Calculation of Column Dimensions

During the trials the reduction factor was determined to be ≥5 for iron and ≥29 for lead. Dividing the maximal values for iron and lead through these factors, the values are inside the present specification of Na$_2$SeO$_3$×5H$_2$O (see Table 4):

TABLE 4

| Metal | Max. values in NaHSeO$_3$ (calculated from SeO$_2$ spec.) (mg/kg) | Divided by reduction factor | Limits NaHSeO$_3$ (calculated from Na$_2$SeO$_3$ × 5H$_2$O spec.) (mg/kg) |
|---|---|---|---|
| Fe | 10.5 | /5 = 2.10 | ≤6.40 |
| Pb | 10.5 | /29 = 0.36 | ≤3.20 |

A column filled with 100 ml resin and loaded with 13 CV (column volumes) NaHSeO3 solution was used to obtain the above indicated reduction factors.

Taking into account the planned volume of NaHSeO$_3$ solution (approx. 21 l) for metal depletion, the exchanger resin volume for the process scale was calculated. Finally 2 l resin has been selected as suitable to purify approx. 26 l, thus including a safety margin of approx. 5 liter. Based on the results obtained from lab scale development the following column configuration and handling parameters were established for production scale metal depletion: Two inline connected columns filled with 1 l resin each; bed height 50 cm, inner diameter 5 cm: linear flow rate 4 CV/h. The resin was intended to be single use and will be discarded after each production run.

During the manufacturing of several pilot batches the sanitisation and rinsing procedure was finally established. For sanitisation with 0.5 M NaOH solution as well as for rinsing off the chromatography system with aqua purificata (AP) flow rates, pressure and conductivity limits have been set. The linear flow rate of loading the columns with NaHSeO$_3$ solution has been slightly modified to 4.2 CV/h corresponding to 70 ml/mm.

c) Synthesis Step 2: pH>10

In order to establish the synthesis step 2 the equivalence point during neutralisation of NaHSeO$_3$ solution, obtained from metal depletion, with NaOH was determined. The experiment was carried out using three different batches of SeO$_2$ for the preparation of three batches of H$_2$SeO$_3$ solution (2.5 mol/l). The solutions were titrated with NaOH solution (4 mol/l). The pH-value was measured after each addition of the NaOH solution. The first equivalence point was determined at approx. pH 5.2 which is not relevant for the synthesis step 1—NaHSeO$_3$ solution, because pH 6.0 is required for carrying out the metal depletion.

The second equivalence point was determined at approx. pH=10.8. With regard to the Ph. Eur. specification for a 10% (mN) Na$_2$SeO$_3$×5 H$_2$O solution of pH=9.8-10.8, the target range was finally set to pH=10.4-10.8.

3. Purification Part 2: Purification of Organic Contaminants
a) Ultrafiltration (UF)

In order to remove low molecular weight organic impurities, e.g. bacterial endotoxins ultrafiltration (cut off: 10 000 daltons) was introduced into the down stream purification process. The ultrafiltration should take place after metal depletion and synthesis step 2 at the stage of the Na$_2$SeO$_3$ solution.

b) Bacterial Filtration (0.5/0.2 μm)

During the preparation of starting solutions for the development of synthesis step 1 at pH=6.0 as well as for the obtained eluates and filtrates from metal depletion, respectively filter combinations were used including a pre-filter (0.5 μm) and a 0.2 μm membrane filter.

Example 2

Crystallization and Drying a) Basic Chemistry

During solubility studies with sodium selenite, J. Janitzki found out that Na$_2$SeO$_3$ exists in three molecular forms. Na$_2$SeO$_3$×8 H$_2$O can be found at deep temperatures up to −8.7° C.

The second form is Na$_2$SeO$_3$×5 H$_2$O which can be received up to 35.9° C. Above this Temperature, water free Na$_2$SeO$_3$ is received during crystallization (see FIG. 1).

J. Janitzki described water free Na$_2$SeO$_3$ as white powder, Na$_2$SeO$_3$×5 H$_2$O as needles or clear prismatic crystals and Na$_2$SeO$_3$×8 H$_2$O also as clear needles. He pointed out, that Na$_2$SeO$_3$×5 H$_2$O looses crystal water in dry air, starting on the surface. [J. Janitzki. Über die selenigsauren Salze des Natriums und des Kaliums; Zeitschrift für anorgan. und allg. Chemie; \'ol. 205. 1932]

A. A. Kudryavtsev described Na$_2$SeO$_3$×5 H$_2$O as white, needle shaped or prismatic crystals, which loose water of crystallization in dry air. [A. A. Kudrvavtsev: The chemistry & technology of Selenium and Telurium; Collet/s LTD; 1974]

L. F. Nilson described Na$_2$SeO$_3$×5 H$_2$O as needles or very large, four-sided prisms. He also pointed out that the crystals are persistent in contact with air. He described water free Na$_2$SeO$_3$ as milk-white, four-sided, quadratic prisms, which are obtained, when crystallization takes place at a higher temperature 60° C.-100° C. [L. F. Nilson; Researches on the salts of Selenious Acid: Upsala: 1875]

b) Evaluation of Influence of Temperature on Na$_2$SeO$_3$×5 H$_2$O

Testing of loss on drying (LOD) at 105° C. until constant weight was reached, has been used during the various trials to determine the identity of Na$_2$SeO$_3$×5 H$_2$O crystals. With respect to the molecular mass, the LOD was calculated to be 34%. Originally the specification for the LOD of $Na_2SeO_3 \times 5\ H_2O$ was set to 30-38%. For the following crystallization/drying trials the target range was limited to 33.0%-35.0%.

In a first series of studies the influence of temperature on $Na_2SeO_3 \times 5\ H_2O$ solid substance was analyzed. Following conditions were applied: 20° C./45% relative humidity, storage time approx. 89 hours. The results showed loss of 1.8% $H_2O$ after 5 h and 4.6% $H_2O$ after 89 h. The total crystal water content was determined to be 34%. The experiment with $Na_2SeO_3 \times 5\ H_2O$ solid substance showed that it already looses part of its hydrate water when it is stored in an unsealed container at 20° C., in combination with a relative humidity of 45%.

It was concluded that $Na_2SeO_3 \times 5\ H_2O$ has to be handled in tightly closed containers and not to be exposed long term to atmospheric conditions.

c) Initial Crystallization/Drying Experiments

The following feasibility studies on crystallization/drying were performed with $Na_2SeO_3$ solutions containing 30% $Na_2SeO_3$ and 70% $H_2O$ (m/m). The density was determined to be approx. 1.34 g/cm³ (20° C.). LOD testing was performed for evaluation of the obtained $Na_2SeO_3$ dry substance.

In a first series of trials several temperature (up to 60° C.) and humidity conditions (25% and 45% rel. humidity) were applied to $Na_2SeO_3$ solutions using a climate cabinet and a desiccator with silica gel. The $Na_2SeO_3$ solution was filled into various types of vessels.

The results obtained led to the conclusion, that this approach is not suitable for producing $Na_2SeO_3 \times 5\ H_2O$ because of the long lasting process time and the non-uniform evaporation of solvent.

Based on the results obtained from the crystallization/drying experiments it was decided to continue the trials employing a fluidised bed dryer and a vacuum paddle dryer, alternatively.

d) Fluidized Bed Dryer and Mechanically Created Fluidized Bed Dryer

During the following described crystallization/drying trials LOD testing was performed for evaluation of the obtained $Na_2SeO_3$ substance on its conformity with the set specification for $Na_2SeO_3 \times 5\ H_2O$ (33.0%-35.0%). In addition LOD was performed using an IR-balance for moisture determination with the advantage to provide the results in very short time compared to the Ph. Eur. method at 105° C. For determination of the $Na_2SeO_3 \times 5\ H_2O$ content a titration according to the European Pharmacopoeia (monograph 1677) was performed (duplicate analysis). The assay is specified as 98.5%-101.5%.

The tests were performed using a lab scale fluidized bed dryer and a 10 l vacuum paddle dryer. $Na_2SeO_3$ solutions for the drying trials contained approx. 30% $Na_2SeO_3$ and 70% $H_2O$ (m/m).

Fluidized Bed Dryer

The bottom spray technique was used during the trials applying fluidized bed technology (0.5 mm nozzle).

The trials with the fluidized bed dryer led to three batches meeting the Ph. Fur. Specification for the $Na_2SeO_3 \times 5\ H_2O$ assay. The results of the assay determination (titration) were confirmed by an additional LOD determination, carried out by using a drying cabinet at 105° C.

The trials showed that $Na_2SeO_3 \times 5\ H_2O$ production would be possible by applying fluidized bed technology. However the tests showed also, that reproducibility is a challenge because the drying conditions have to be controlled very precisely. For instance the moisture of the inlet air should be adjustable as well as cooling of the inlet air in case of high environmental temperature should be established. Those sensitive parameters can only be controlled by a PLC system (program logic control) including computer hardware and software. In addition a fluidised bed has to be created before spraying of the $Na_2SeO_3$ solution is possible. That means for the manufacturing of each batch a certain amount of $Na_2SeO_3 \times 5\ H_2O$ from another batch has to be placed in the dryer, which would lead to a mixture of different batches.

Vacuum Paddle Dryer

During the experimental phase employing the vacuum paddle dryer, four different batches have been prepared in the range of 5-7 liter $Na_2SeO_3$ solution.

For each trial the solution was filled into the vacuum paddle dryer and subsequently the drying was performed in several stages. Applying heat exchanger medium temperatures between 25° C.-40° C. and vacuum in the range of 10-100 mbar. In addition, rotation speed and rotation direction of the stirring paddle was modified during the various stages of drying. Vacuum and product temperature were recorded.

From the first trial with a filling volume of 5 liter $Na_2SeO_3$ solution dry substance was obtained with an LOD of 33.3%, which was within the target range of 33.0%-35.0%. However, an unacceptable amount of dry substance stuck on the wall, paddles and spindle of the paddle dryer. The result obtained from the first trial could be confirmed by the following three trials, whereas the drying times were significantly longer caused by application of a vacuum pump with less pumping speed.

The trials with the vacuum paddle dryer showed that the usage of a paddle dryer works in principle. Nevertheless, too much product stuck on the paddle dryer, especially on the paddles. This would not be acceptable for routine production.

Mechanical Fluidized Bed in Vacuum Paddle Dryer

Based on the experience and the results obtained during the trials employing the fluidized bed technology and vacuum drying under mechanical agitation a new crystallization/drying concept was established. The improved process was designed to employ a "mechanical fluidized bed" created in a customized built vacuum paddle dryer. For proof of the new concept a preliminary trial was carried out using a modified vacuum paddle dryer. The trial was carried out by spraying the $Na_2SeO_3$ solution into the empty paddle dryer under mechanical agitation. During the initial phase formation of seed crystals occurred and subsequently at 0-20 mbar and temperatures between 20° C. and 30° C. the crystallization/drying was performed. The obtained dry substance was within the target range of $Na_2SeO_3 \times 5\ H_2O$ and conforms to the specification of content "titration according to the European Pharmacopoeia (monograph 1677)". The recovery of the product was significantly improved and thus within an acceptable range.

Scale Up of the Entire Manufacturing Process

After delivery and qualification of the customized built vacuum paddle dryer several full scale pilot batches were manufactured.

The batch size of the starting $Na_2SeO_3$ solution was finally set to 20.5 l with a concentration of 2.5 mol/l. During synthesis step I and synthesis step 2 cooling of the solution was introduced to reduce the increased temperature created by the exothermic reaction with NaOH. Stirring conditions and the filtration flow rate of 1 l/min for the 0.5/0.2 membrane filtration were established. Scale up of the metal depletion and the ultrafiltration process was performed as described in the relevant sections above. IPC was established for the various process steps and intermediate solutions, respectively. At that stage target ranges for, e.g. density, pH, conductivity, content of dry substance, bacterial endotoxins, bioburden and filter integrity tests were set.

The crystallization/drying process was established on the vacuum paddle dryer. The process conditions, e.g. spraying volume of the $Na_2SeO_3$ solution, temperature of the heat exchange medium, pressure range and process times during initial, main and post drying were finally defined. The IPC loss on drying was introduced to get information about the progress on drying during post drying phases.

Finally, samples from the obtained final product were tested according to the established quality control methods, in order to determine the conformity of $Na_2SeO_3 \times 5\ H_2O$ to the specification.

Example 3

Quality Control

In the following tables the specifications of sodium selenite pentahydrate and the test results of sodium selenite pentahydrate obtained by the method of the present invention are presented.

The following purity specifications were established according to Ph. Eur. requirements: clarity, colour and pH-value of testing solution, loss on drying, limit test on chloride, limit test on sulphate, selenate and limit test on iron.

The heavy metals (iron, nickel, copper, cadmium, lead, tellurium, arsenic and silver are determined by AAS, whereas mercury is determined by ICP-MS.

The biological safety is tested with the test on bacterial endotoxins and with microbial enumeration test and test for specific micro-organisms in accordance with Ph. Eur.

The content of sodium selenite pentahydrate is tested according to the Ph. Eur. monograph. For determination of sodium and selenium a AAS is used.

Validations of analytical methods have been made for the methods which have not been determinated according to Ph. Eur.

The general properties of sodium selenite pentahydrate are performed by visual test of appearance of the powder.

The identity of sodium selenite pentahydrate is verified by two identity tests for selenite and one for sodium according to Ph. Eur. requirements. Additionally selenium is identified by a chemical reaction with diphenylhydrazine.

TABLE 5 selenite pentahydrate release specifications:

| PARAMETER | METHOD | SPECIFICATION |
|---|---|---|
| General Properties | | |
| Appearance | Visual inspection | White or almost white, crystalline powder, hygroscopic |
| Identity | | |
| Selenite | Ph. Eur. 1677 | Forming of a red precipitate after addition of ascorbic acid which may become black |
| Selenium | Chemical reaction | Forming of a violet colour after addition of diphenylhydrazine |
| Selenite | Ph. Eur. 1677 | Testing solution remains clear after addition of $BaCl_2$ |
| Sodium | Ph. Eur. 2.3.1 a | Gives reaction of sodium |
| Purity | | |
| Clarity of testing solution (10% m/V) | Ph. Eur. 2.2.1 | Testing solution is clear |
| Colour of testing solution (10% m/V) | Ph. Eur. 2.2.2, method II | Testing solution is colourless |
| pH-value of testing solution (10% m/V) | Ph. Eur. 2.2.3 | 9.8-10.8 |
| Loss on drying | Ph. Eur. 2.2.32 | 32-36% (m/m) |
| Limit test chloride | Ph. Eur. 2.4.4 | ≤50 ppm |
| Limit test sulphate, selenate | Ph. Eur. 2.4.13 | ≤300 ppm (determined as sulphate) |
| Limit test iron | Ph. Eur. 1677 | ≤50 ppm |
| Iron | AAS | ≤10 ppm |
| Nickel | AAS | ≤5 ppm |
| Copper | AAS | ≤5 ppm |
| Cadmium | AAS | ≤5 ppm |
| Lead | AAS | ≤5 ppm |
| Tellurium | AAS | ≤300 ppm |
| Arsenic | AAS | ≤20 ppm |
| Silver | AAS | ≤5 ppm |
| Mercury | ICP-MS | ≤5 ppm |
| Residual solvents | Ph. Eur. 5.4 | Excluded due to manufacturing process |
| Content | | |
| Sodium selenite pentahydrate | Ph. Eur. 1677 | 98.5-101.5% |
| Sodium | AAS | 25.3-27.9% (referred to dry substance) |
| Selenium | AAS | 43.4-47.9% (referred to dry substance) |
| Biological Safety | | |
| Bacterial endotoxins | Ph. Eur. 2.6.14, method C | ≤1,000 I.U./g |
| Bacteria (TAMC) | Ph. Eur. 2.6.12 | ≤1,000 cfu/g |
| Yeast/mould (TYMC) | Ph. Eur. 2.6.12 | ≤100 cfu/g |

TABLE 5-continued selenite pentahydrate release specifications:

| PARAMETER | METHOD | SPECIFICATION |
|---|---|---|
| Enterobacteria | Ph. Eur. 2.6.13 | ≤1 cfu/g |
| *Escherichia coli* | Ph. Eur. 2.6.13 | Not detectable/g |
| *Salmonalla* | Ph. Eur. 2.6.13 | Not detectable/10 g |
| *Pseudomonas aeruginosa* | Ph. Eur. 2.6.13 | Not detectable/g |
| *Staphylococcus aureus* | Ph. Eur. 2.6.13 | Not detectable/g |

Table 6 shows that the release specifications are met by sodium selenite pentahydrate obtained by the method of the present invention as exemplified in Examples 1 and 2 above.

TABLE 6

Scheme about the batch results of three production batches of sodium selenite pentahydrate:

| | | Batch no. | | |
|---|---|---|---|---|
| PARAMETER | SPECIFICATION | 927260 | 928262 | 930277 |
| Batch size | | 10 kg | 10 kg | 10 kg |
| Manufacturing site | | biosyn Arzneimittel GmbH | | |
| General Properties | | | | |
| Appearance | White or almost white, crystalline powder, hygroscopic | White, crystalline powder, hygroscopic | White, crystalline powder, hygroscopic | White, crystalline powder, hygroscopic |
| Identity | | | | |
| Selenite | Forming of a red precipitate after addition of ascorbic acid which may become black | Forming of a red precipitate after addition of ascorbic acid which became black | Forming of a red precipitate after addition of ascorbic acid which became black | Forming of a red precipitate after addition of ascorbic acid which became black |
| Selenium | Forming of a violet colour after addition of diphenylhydrazine | Forming of a violet colour after addition of diphenylhydrazine | Forming of a violet colour after addition of diphenylhydrazine | Forming of a violet colour after addition of diphenylhydrazine |
| Selenite | Testing solution remains clear after addition of $BaCl_2$ | Testing solution remains clear after addition of $BaCl_2$ | Testing solution remains clear after addition of $BaCl_2$ | Testing solution remains clear after addition of $BaCl_2$ |
| Sodium | Gives reaction of sodium | Gives reaction of sodium | Gives reaction of sodium | Gives reaction of sodium |
| Purity | | | | |
| Clarity of testing solution (10% m/V) | Testing solution is clear | Testing solution is clear | Testing solution is clear | Testing solution is clear |
| Colour of testing solution (10% m/V) | Testing solution is colourless | Testing solution is colourless | Testing solution is colourless | Testing solution is colourless |
| pH-value of testing solution (10% m/V) | 9.8-10.8 | 10.4 | 10.6 | 10.6 |
| Loss on drying | 32-36% (m/m) | 33% (m/m) | 33% (m/m) | 34% (m/m) |
| Limit test chloride | ≤50 ppm | <50 ppm | <50 ppm | <50 ppm |
| Limit test sulphate, selenate | ≤300 ppm (determined as sulphate) | <300 ppm | <300 ppm | <300 ppm |
| Limit test iron | ≤50 ppm | <50 ppm | <50 ppm | <50 ppm |
| Iron | ≤10 ppm | <10 ppm | <10 ppm | <10 ppm |
| Nickel | ≤5 ppm | <2.5 ppm | <2.5 ppm | <2.5 ppm |
| Copper | ≤5 ppm | <5 ppm | <5 ppm | <5 ppm |
| Cadmium | ≤5 ppm | <2.5 ppm | <2.5 ppm | <2.5 ppm |
| Lead | ≤5 ppm | <5 ppm | <2.5 ppm | <2.5 ppm |
| Tellurium | ≤300 ppm | <150 ppm | <150 ppm | <150 ppm |
| Arsenic | ≤20 ppm | <10 ppm | <10 ppm | <10 ppm |

TABLE 6-continued

Scheme about the batch results of three production batches of sodium selenite pentahydrate:

| PARAMETER | SPECIFICATION | Batch no. 927260 | Batch no. 928262 | Batch no. 930277 |
|---|---|---|---|---|
| Silver | ≤5 ppm | <2.5 ppm | <2.5 ppm | <2.5 ppm |
| Mercury | ≤5 ppm | <2.5 ppm | <2.5 ppm | <2.5 ppm |
| Residual solvents | Excluded due to manufacturing process | Excluded due to manufacturing process | Excluded due to manufacturing process | Excluded due to manufacturing process |
| Content | | | | |
| Sodium selenite pentahydrate | 98.5-101.5% | 99.9% | 100.3% | 100.7% |
| Sodium | 25.3-27.9% (referred to dry substance) | 26.3% | 26.3% | 26.5% |
| Selenium | 43.4-47.9% (referred to dry substance) | 45.5% | 45.0% | 45.0% |
| Biological Safety | | | | |
| Bacterial endotoxins | ≤1,000 I.U./g | <100 I.U./g | <100 I.U./g | <100 I.U./g |
| Bacteria (TAMC) | ≤1,000 cfu/g | <1 cfu/g | <1 cfu/g | <1 cfu/g |
| Yeast/mould (TYMC) | ≤100 cfu/g | <1 cfu/g | <1 cfu/g | <1 cfu/g |
| Enterobacteria | ≤1 cfu/g | <1 cfu/g | <1 cfu/g | <1 cfu/g |
| *Escherichia coli* | Not detectable/g | Not detectable/g | Not detectable/g | Not detectable/g |
| *Salmonalla* | Not detectable/10 g | Not detectable/10 g | Not detectable/10 g | Not detectable/10 g |
| *Pseudomonas aeruginosa* | Not detectable/g | Not detectable/g | Not detectable/g | Not detectable/g |
| *Staphylococcus aureus* | Not detectable/g | Not detectable/g | Not detectable/g | Not detectable/g |

The data above show that the three production batches exemplified comply with the release specifications.

Stability studies according to ICH requirements with 3 production batches were also conducted.

The batches are tested at long term storage conditions at 25° C.±2° C. and 60%±5% relative humidity (r.h.) over a period of 60 months.

Since the transformation point of sodium selenite pentahydrate into anhydrous sodium selenite is at 36° C., the batches will not be tested at accelerated storage conditions of 40° C.±2° C. and 75%±5% r.h.

The 3 production batches will be tested additionally at intermediate storage conditions 30° C.±2° C. and 65%±5% r.h. over a period of 12 months.

Additionally an in-use stability study with 2 production batches in the primary and secondary packaging material is in progress.

At present 3 months stability data of one batch of the in-use stability study are available, where all parameters are well within required shelf-life specifications (Table 7).

TABLE 7

Stability data of sodium selenite pentahydrate

| Test (Method) | Shelf-life Specification | Initial | 1 month | 2 months | 3 months |
|---|---|---|---|---|---|
| Appearance (visual inspection) | white to almost white, crystalline, hygroscopic powder | conforms | conforms | conforms | conforms |
| Clarity of testing solution (10% m/V) (Ph. Eur. 2.2.1) | clear | clear | clear | clear | clear |
| Colour of testing solution (10% m/V) (Ph. Eur. 2.2.2, method II) | colorless | colorless | colorless | colorless | colorless |
| pH-value of testing solution (10% m/V) (Ph. Eur. 2.2.3) | 9.8-10.8 | 10.4 | 10.5 | 10.5 | 10.5 |
| Loss on drying (Ph. Eur. 2.2.32) | 32-36% | 33.2 | 33.3 | 33.1 | 33.1 |
| Limit test sulphate, selenate (Ph. Eur. 2.4.13) | </=300 ppm | <300 | <300 | <300 | <300 |
| Sodium Selenite Pentahydrate (Ph. Eur. 1677) | 98.5-101.5% | 99.9 | 100.6 | 100.6 | 99.8 |
| Sodium (AAS) | 25.3-27.9% (referred to dry substance) | 26.3 | 26.0 | 26.3 | 27.0 |

TABLE 7-continued

Stability data of sodium selenite pentahydrate

| Test (Method) | Shelf-life Specification | Initial | 1 month | 2 months | 3 months |
|---|---|---|---|---|---|
| Selenium (AAS) | 43.4-47.9% (referred to dry substance) | 45.5 | 46.8 | 46.3 | 45.0 |
| Bacterial endotoxins (Ph. Eur. 2.6.14, method C) | </=1000 I.U./g | <100 | — | — | — |
| Bacteria (TAMC, Ph. Eur. 2.6.12) | </=1000 cfu/g | <1 | — | — | — |
| Yeast/mould (TYMC, Ph. Eur. 2.6.12) | </=100 cfu/g | <1 | — | — | — |
| Enterobacteria (Ph. Eur. 2.6.13) | </=1 cfu/g | <1 | — | — | — |
| *Escherichia coli* (Ph. Eur. 2.6.13) | not detectable/g | conforms | — | — | — |
| *Salmonella* | not detectable/10 g | conforms | — | — | — |
| *Pseudomonas aeruginosa* (Ph. Eur. 2.6.13) | not detectable/g | conforms | — | — | — |
| *Staphylococcus aureus* (Ph. Eur. 2.6.13) | not detectable/g | conforms | — | — | — |

The invention claimed is:

1. A process for manufacturing a crystalline substance comprising the steps of
   a) delivering an unsaturated solution of the substance to be crystallized into a fluidized bed dryer, under pressure and temperature conditions of applying a vacuum and maintaining a temperature range, in order to dry the solution of a substance to be crystallized to thereby obtain a supersaturated solution, in which crystallization takes place, and
   b) applying vacuum and maintaining a temperature range in the fluidized bed dryer after completion of the step of delivering the unsaturated solution of the substance to be crystallized, wherein the vacuum and the temperature are regulated in a manner in order to obtain the desired crystalline product as a homogenous product,
   wherein the crystalline substance is an inorganic or organic salt.

2. The process of claim 1, wherein the method does not contain a step of adding a seed crystal.

3. The process of claim 1, wherein in step a) the unsaturated solution is delivered by spraying, pumping or sprinkling.

4. The process of claim 1, wherein the unsaturated solution of the substance to be crystallized is delivered into a fluidized bed dryer, which is a mechanically created fluidized bed dryer, wherein the crystallization takes place under mechanical agitation.

5. The process of claim 1, wherein the temperature and/or vacuum are controlled in step a) and b).

6. The process of claim 5, wherein the temperature and/or vacuum are controlled in step a) and b) in order to avoid sticking of dry substance to the surface of the fluidized bed dryer.

7. The process of claim 1, further comprising
   c) adding an amount of free solvent into the fluidized bed dryer, and/or
   d) regulating pressure and temperature before removing the crystalline substance from the fluidized bed.

8. The process of claim 1, wherein the crystalline substance is a pharmaceutical.

9. The process of claim 1, wherein in step a) the unsaturated solution is delivered by spraying.

10. The process of claim 1, wherein the inorganic or organic salt is a selenium salt.

11. The process of claim 10, wherein the selenium salt is a hydrate of $Na_2SeO_3$.

12. The process of claim 11, wherein the selenium salt is $Na_2SeO_3 \times 5H_2O$.

13. A device for manufacturing a crystalline substance, which comprises
   a) a fluidized bed dryer in a vacuum vessel,
   b) inlet means for transporting an unsaturated solution of the raw substance to be crystallized into the vacuum vessel,
   c) means for temperature regulating,
   d) a spraying device for introducing the unsaturated solution into the fluidized bed dryer,
   e) outlet means for transporting vapor out of the vacuum vessel, and
   f) discharge means for removing the crystalline substance out of the vacuum vessel.

14. The device of claim 13, wherein the fluidized bed dryer is a mechanically induced fluidized bed dryer.

15. The device of claim 14, wherein the inlet means comprises a feed piping (1), a feed pump (2) and/or a flow meter (3).

16. The device of claim 14, wherein the mechanically induced fluidized bed dryer comprises one or more mixing elements (7, 8).

17. The device of claim 13, wherein the outlet means comprise a vapor dome housing (9), a built-in pulse back dust filter (10), a vacuum pipe to a vacuum pump (11) and/or a nitrogen supply (12).

18. The device of claim 13 further comprising means for measuring temperature, pressure and humidity in the vacuum vessel.

19. A process for producing a crystalline substance comprising the use of the device of claim 13.

* * * * *